United States Patent
Hsieh et al.

(10) Patent No.: US 10,842,421 B2
(45) Date of Patent: Nov. 24, 2020

(54) SENSING DEVICE, NURSING BRA, AND MANUFACTURING METHOD THEREOF

(71) Applicant: Winbond Electronics Corp., Taichung (TW)

(72) Inventors: Ming-Hung Hsieh, Taichung (TW); Yu-Hsuan Ho, Taichung (TW); Ming-Chih Tsai, Taichung (TW); Yen-Jui Chu, Taichung (TW)

(73) Assignee: Winbond Electronics Corp., Taichung (TW)

( * ) Notice: Subject to any disclaimer, the term of this patent is extended or adjusted under 35 U.S.C. 154(b) by 226 days.

(21) Appl. No.: 15/700,196

(22) Filed: Sep. 11, 2017

(65) Prior Publication Data

US 2018/0160952 A1    Jun. 14, 2018

(30) Foreign Application Priority Data

Dec. 12, 2016  (CN) .......................... 2016 1 1137245

(51) Int. Cl.

| | |
|---|---|
| *A61B 5/00* | (2006.01) |
| *A61B 5/145* | (2006.01) |
| *A61B 5/1468* | (2006.01) |
| *G01N 27/333* | (2006.01) |
| *C12M 1/34* | (2006.01) |
| *G01N 27/06* | (2006.01) |
| *A61B 5/01* | (2006.01) |

(52) U.S. Cl.
CPC ............ *A61B 5/14546* (2013.01); *A61B 5/01* (2013.01); *A61B 5/1468* (2013.01); *A61B 5/14507* (2013.01); *A61B 5/4312* (2013.01); *A61B 5/6804* (2013.01); *A61B 5/6823* (2013.01); *C12M 41/32* (2013.01); *G01N 27/06* (2013.01); *G01N 27/333* (2013.01); *A61B 5/14539* (2013.01)

(58) Field of Classification Search
CPC combination set(s) only.
See application file for complete search history.

(56) References Cited

U.S. PATENT DOCUMENTS

| | | | |
|---|---|---|---|
| 2007/0114138 A1 | 5/2007 | Krasteva et al. | |
| 2009/0242429 A1* | 10/2009 | Sitdikov | B82Y 5/00 |
| | | | 205/792 |
| 2011/0140703 A1 | 6/2011 | Chiao et al. | |
| 2016/0313306 A1* | 10/2016 | Ingber | C12M 21/08 |

FOREIGN PATENT DOCUMENTS

| | | | | |
|---|---|---|---|---|
| CN | 101676714 | | 3/2010 | |
| TW | 200839235 | | 10/2008 | |
| TW | 201617585 | | 5/2016 | |
| WO | WO-2016090189 A1 * | | 6/2016 | ........... A61B 5/6833 |

* cited by examiner

*Primary Examiner* — Paul S Hyun
(74) *Attorney, Agent, or Firm* — JCIPRNET

(57) ABSTRACT

A sensing device for sensing ion concentration of a solution, including a first substrate, a second substrate, a sensing layer, and two electrodes. The material of the first substrate includes cellulose. The second substrate is located on the first substrate. The sensing layer is located on the second substrate. The two electrodes are separately disposed on the sensing layer to expose the sensing layer and bring a solution in contact with the sensing layer so as to measure the resistance value of the solution and convert the resistance value into the ion concentration of the solution.

14 Claims, 2 Drawing Sheets

SENSING DEVICE, NURSING BRA, AND MANUFACTURING METHOD THEREOF

CROSS-REFERENCE TO RELATED APPLICATION

This application claims the priority benefit of China application serial no. 201611137245.4, filed on Dec. 12, 2016. The entirety of the above-mentioned patent application is hereby incorporated by reference herein and made a part of this specification.

BACKGROUND OF THE INVENTION

Field of the Invention

The invention relates to a sensing device and a manufacturing method thereof, and more particularly to a sensing device applied in a nursing bra and a manufacturing method thereof.

Description of Related Art

During women's lactation stage, if cleaning is not sufficiently performed or breast milk is not emptied, lactiferous duct blockage or mastitis readily occurs to the breasts, thus the breasts may have the symptoms such as redness and swelling, stiffness, pain, or hotness.

Currently, research on disposing a temperature sensor in women's undergarment to sense the phenomenon of abnormal rise in local body temperature has been conducted. However, generally, when the body temperature is raised abnormally, symptoms of lactiferous duct blockage or mastitis have already occurred, and therefore the symptoms cannot be prevented. Therefore, how to effectively prevent the symptoms of lactiferous duct blockage or mastitis is one of the pressing issues to be solved in the industry.

SUMMARY OF THE INVENTION

An embodiment of the invention provides a sensing device and a manufacturing method thereof, wherein the sensing device has the function of measuring ion concentration of a solution and the characteristic of being readily integrated on a non-planar substrate.

An embodiment of the invention provides a nursing bra sensing device and a manufacturing method thereof, wherein the nursing bra sensing device has the function of monitoring ion concentration of breast milk to effectively prevent symptoms of lactiferous duct blockage or mastitis.

An embodiment of the invention provides a sensing device for sensing ion concentration of a solution, including a first substrate, a second substrate, a sensing layer, and two electrodes. The material of the first substrate includes cellulose. The second substrate is located on the first substrate. The sensing layer is located on the second substrate. The two electrodes are separately disposed on the sensing layer to expose the sensing layer and bring the solution in contact with the sensing layer so as to measure the resistance value of the solution. The ion concentration of the solution can be obtained after the conversion of the resistance value.

In an embodiment of the invention, the sensing device further includes an insulating layer located between the second substrate and the sensing layer.

In an embodiment of the invention, the sensing device further includes a protective layer covering the top surfaces and sidewalls of the two electrodes.

In an embodiment of the invention, the ion includes sodium ion, potassium ion, or a combination thereof.

In an embodiment of the invention, the concentration range of the sodium ion is between 10 mmol/L and 25 mmol/L.

In an embodiment of the invention, the concentration range of the potassium ion is between 5 mmol/L and 20 mmol/L.

In an embodiment of the invention, the material of the sensing layer includes metal oxide.

In an embodiment of the invention, the metal oxide includes tin oxide, zinc oxide, tungsten oxide, titanium oxide, iron oxide, chromium oxide, indium tin oxide, indium zinc oxide, or a combination thereof.

An embodiment of the invention provides a nursing bra for sensing ion concentration of breast milk, wherein the nursing bra includes two cup portions, a connecting portion, two breast milk absorbing pads, and two of the sensing device above. The two cup portions are respectively disposed at locations corresponding to human breasts. The connecting portion is connected between the two cup portions. The two breast milk absorbing pads are respectively located on the inner side of the two cup portions. The two sensing devices are respectively disposed on the two breast milk absorbing pads.

In an embodiment of the invention, a transmission device located on the inner side of the connecting portion is further included, wherein the transmission device is used to output the data of the two sensing devices.

The invention provides a manufacturing method of a sensing device suitable for sensing the ion concentration of a solution, including the following steps. A first substrate is provided, wherein the material of the first substrate includes cellulose. A second substrate is formed on the first substrate. A sensing layer is formed on the second substrate. Two electrodes separated from each other are formed on the sensing layer to expose the sensing layer and bring the solution in contact with the sensing layer so as to measure the resistance value of the solution. The ion concentration in the solution can be obtained after the conversion of the resistance value.

In an embodiment of the invention, the method of providing the first substrate and the second substrate, the forming method of the sensing layer, and the two electrodes include 3D printing.

In an embodiment of the invention, an insulating layer is formed on the second substrate before the step of forming the sensing layer, wherein the insulating layer is located between the second substrate and the sensing layer.

In an embodiment of the invention, a protective layer is further formed after the two electrodes are formed, wherein the protective layer covers the top surfaces and sidewalls of the two electrodes.

An embodiment of the invention provides a manufacturing method of a nursing bra suitable for sensing the ion concentration of breast milk, including the following steps. Two breast milk absorbing pads are respectively disposed on the inner side of two cup portions of the nursing bra, wherein the two cup portions are respectively located at locations corresponding to human breasts. The manufacturing method of a sensing device is respectively performed on the two breast milk absorbing pads to form two sensing devices.

In an embodiment of the invention, a transmission device is further disposed on the inner side of a connecting portion connected between the two cup portions, wherein the transmission device is used to output the data of the two sensing devices.

Based on the above, the sensing device of the invention is obtained by a 3D printing method, and therefore the sensing device is readily formed on a non-planar substrate. Moreover, the sensing device of the invention has the function of measuring the resistance value of a solution, and the ion concentration of the solution can be obtained via conversion. Therefore, in the invention, by integrating the sensing device in the nursing bra, the concentration of sodium ion or potassium ion in breast milk can be monitored at any time, such that women can know when to perform cleaning or empty the breast milk during the lactation stage to effectively prevent symptoms of lactiferous duct blockage or mastitis.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
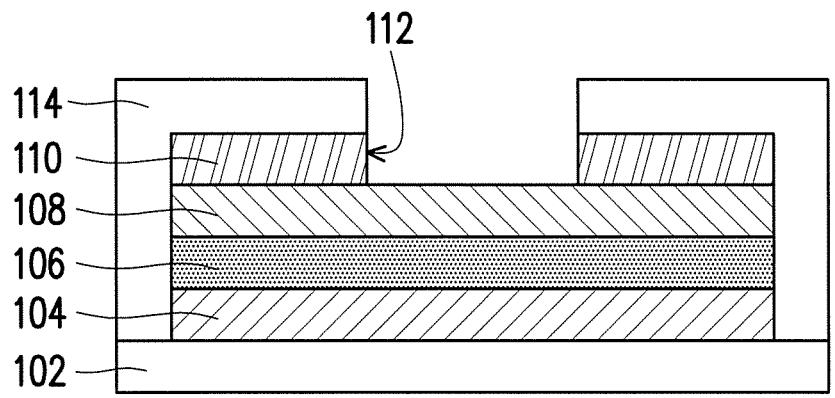
FIG. 1 is a cross-sectional schematic diagram of a sensing device according to an embodiment of the invention.

FIG. 1 is a cross-sectional schematic diagram of a sensing device according to an embodiment of the invention.

Referring to FIG. 1, a sensing device 100 of an embodiment of the invention includes a first substrate 102, a second substrate 104, an insulating layer 106, a sensing layer 108, two electrodes 110, and a protective layer 114. The first substrate 102 is, for instance, a flexible substrate. In some embodiments, the surface of the first substrate 102 is a planar surface. In some other embodiments, the surface of the first substrate 102 is a non-planar surface. For instance, the surface of the first substrate 102 can be curved, concave, uneven, slanted, or a combination thereof. The method of forming the first substrate 102 includes an imprinting method, a vacuum filtration method, a 3D printing method, or a combination thereof. In other embodiments, the first substrate 102 can be a porous material having pores. For instance, the material of the first substrate 102 can be cellulose such as nanocellulose, polyethylene terephthalate (PET), polyethylene naphthalate (PEN), polyimide (PI), or a combination thereof.

The second substrate 104 can be optionally located on the first substrate 102. In some embodiments, the sensing device 100 can have the second substrate 104. In some other embodiments, the sensing device 100 may not have the second substrate 104. The material of the second substrate 104 and the material of the first substrate 102 are different, and the material of the second substrate 104 is, for instance, metal, polymer, a silicon layer, or a combination thereof. The method of forming the second substrate 104 is, for instance, a chemical vapor deposition method (CVD), a 3D printing method, an inkjet printing method, or a combination thereof.

In the embodiment in which the first substrate 102 is a porous material, the second substrate 104 can extend to the pores of the first substrate 102. As a result, the adhesion between the first substrate 102 and the second substrate 104 can be increased to improve the stability of the sensing device 100.

The insulating layer 106 is located on the second substrate 104 to block moisture and prevent the issue of short-circuit caused by dust intrusion. Moreover, the insulating layer 106 can also prevent ion or metal ion contamination. More specifically, when the sensing device 100 senses a solution containing sodium ions, potassium ions or metal ions, the insulating layer 106 can make it difficult for the ions in the solution to enter the second substrate 104 or the first substrate 102, and therefore ion or metal ion contamination can be prevented, such that the sensing device 100 has good durability. The insulating layer 106 can be a single layer or a multilayer. The material of the insulating layer 106 can be inorganic material or organic material. The inorganic material can be oxide, nitride, oxynitride, or a combination thereof, such as silicon oxide, silicon nitride, silicon oxynitride, or a combination thereof. The organic material can be tetraethyl orthosilicate (TEOS), polymethylmethacrylate (PMMA), or a combination thereof. The method of forming the insulating layer 106 is, for instance, a chemical vapor deposition method, a 3D printing method, an inkjet printing method, or a combination thereof.

The sensing layer 108 is located on the insulating layer 106. The material of the sensing layer 108 can be, for instance, metal oxide. For instance, the metal oxide can be tin oxide ($SnO_2$), zinc oxide (ZnO), tungsten oxide ($WO_3$), titanium oxide ($TiO_2$), iron oxide ($Fe_2O_3$), chromium oxide ($ZrO_2$), indium tin oxide (ITO), indium zinc oxide (IZO), or a combination thereof. The method of forming the sensing layer 108 is, for instance, a chemical vapor deposition method, a 3D printing method, an inkjet printing method, or a combination thereof.

The two electrodes 110 are separately disposed on the sensing layer 108 to expose the sensing layer 108. As a result, the solution to be measured can enter from an opening 112 between the two electrodes 110 and contact with the surface of the sensing layer 108, therefore the change of the ion concentration of the solution to be measured can be calculated by measuring the changes of, for instance, the resistance, conductivity, current, and voltage between the two electrodes 110. In the present embodiment, the sensing device 100 calculates the concentration of the sodium ions and the potassium ions in the solution by measuring the resistance or the conductivity, but the invention is not limited thereto. In an exemplary embodiment, the sensing device 100 can measure the sodium ion concentration ranging between 10 mmol/L and 25 mmol/L and the potassium ion concentration ranging between 5 mmol/L and 20 mmol/L.

Figure 2:
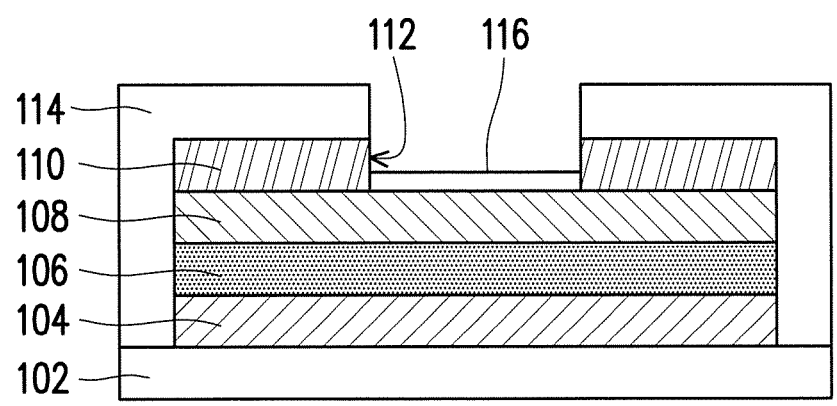
FIG. 2 is a cross-sectional schematic diagram of a sensing device according to another embodiment of the invention.

In an embodiment, a modified layer 116 (as shown in FIG. 2) can also be disposed on the sensing layer 108 between the two electrodes 110 to increase the selectivity of the sensing device 100. For instance, the modified layer 116 can be an ion-selective layer. More specifically, the ion selective layer can be a negatively-charged film, so that negatively-charged ions (such as chlorine ions) in the solution do not readily come close to the surface of the sensing layer 108. As a result, the sensing layer 108 can be targeted to sense positively-charged ions (such as sodium ions or potassium ions) to increase the selectivity of the sensing device 100. The material of the modified layer 116 can be Nafion®, chitosan, or a combination thereof. The method of forming the modified layer 116 can be a 3D printing method, an inkjet method, a drop casting method, or a combination thereof.

The protective layer 114 covers the top surfaces and the outer sidewalls of the two electrodes 110 to prevent the two electrodes 110 from scratching. In an embodiment, the protective layer 114 can also optionally cover the inner and outer sidewalls of the two electrodes 110. In the present embodiment, the protective layer 114 not only covers the top surfaces and the outer sidewalls of the two electrodes 110, but also covers the two sidewalls of the sensing layer 108, the insulating layer 106, and the second substrate 104 and the top surface of the first substrate 102, but the invention is not limited thereto. The material of the protective layer 114 can be polyimide (PI), silicon nitride (SiN), or a combination thereof. The method of forming the protective layer 114 is, for instance, a 3D printing method, an inkjet printing method, or a combination thereof. The "outer sidewalls of the two electrodes 110" represents the sidewalls of the two electrodes 110 which are away from the opening 112.

It should be mentioned that, the temperature of the solution and the corresponding resistance value or conductivity thereof are related. In other words, the resistance value and conductivity of the same solution are different at different temperatures. Therefore, in an embodiment, when the second substrate 104 is a temperature sensing layer, and the relationship between the temperature and the resistance value is known, the resistance value at the temperature at that time can be accurately sensed to prevent errors caused by temperature change.

Still referring to FIG. 1, the manufacturing method of the sensing device 100 of an embodiment of the invention includes the following steps. A first substrate 102 is provided. A second substrate 104, an insulating layer 106, a sensing layer 108, and two electrodes 110 separated from each other are formed on the first substrate 102 in order. The two electrodes 110 separated from each other expose a portion of the sensing layer 108 such that the solution can be in contact with the surface of the sensing layer to measure the resistance value of the solution, and the resistance value can be converted into the ion concentration of the solution. Moreover, a protective layer 114 can also be formed on the two electrodes 110 to cover the top surfaces and the outer sidewalls of the two electrodes 110.

In an embodiment, the method of providing the first substrate 102, the method of forming the second substrate 104, the method of forming the sensing layer 108, the method of forming the insulating layer 106, the method of foiling the two electrodes 110, and the method of forming the protective layer 114 include a 3D printing method, an inkjet printing method, or a combination thereof, wherein the 3D printing method or inkjet printing method readily forms the first substrate 102, the second substrate 104, the insulating layer 106, the sensing layer 108, the two electrodes 110, and the protective layer 114 on a curved surface, concave surface, slanted surface, a combination thereof, or a similar surface, which is not readily achieved by a known semiconductor manufacturing method.

Moreover, in the invention, the sensing device 100 can be formed by a 3D printing method, and therefore the sensing device 100 is readily formed on various substrates and has broad applicability. In the invention, the sensing device 100 is applied in a nursing bra and the ion concentration of breast milk is monitored for early detection of signs of lactiferous duct blockage or mastitis, but the invention is not limited thereto. For instance, the sensing device 100 can also be applied in a general undergarment to monitor the body surface temperature of the breasts for early detection of signs of breast cancer.

Figure 3:
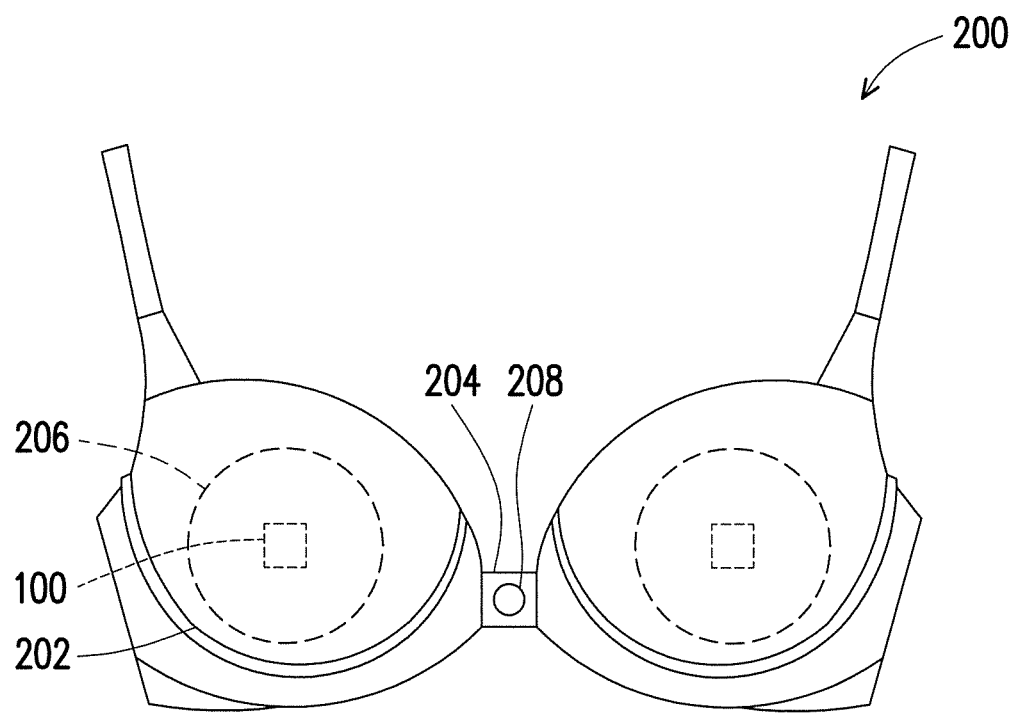
FIG. 3 is a schematic diagram of a nursing bra according to an embodiment of the invention.

FIG. 3 is a schematic diagram of a nursing bra according to an embodiment of the invention.

Referring to FIG. 3, a nursing bra 200 of an embodiment of the invention includes two cup portions 202, a connecting portion 204, two breast milk absorbing pads 206, and a sensing device 100. The two cup portions 202 are respectively disposed at locations corresponding to human breasts. The material of the two cup portions 202 can be, for instance, fluorine-containing fiber, polyurethane resin, nylon fiber, or a combination thereof.

The connecting portion 204 is located between the two cup portions 202 to connect the two cup portions 202. In an embodiment, a transmission device 208 can also be disposed on the connecting portion 204 to output the data measured by the sensing device 100. The transmission device 204 can be, for instance, a wireless transmission device. For instance, the wireless transmission device can be Bluetooth, Zigbee, ultra-wideband (UWB), or a combination thereof. In the present embodiment, the transmission device 208 is located on the inner side of the connecting portion 204, but the invention is not limited thereto. For instance, the transmission device 208 can also be located on the outer side of the connecting portion 204 or at other locations of the nursing bra 200. The "inner side of the connecting portion 204" represents the side of the connecting portion 204 adjacent to the skin. The "outer side of the connecting portion 204" represents the side of the connecting portion 204 away from the skin.

Figure 4:
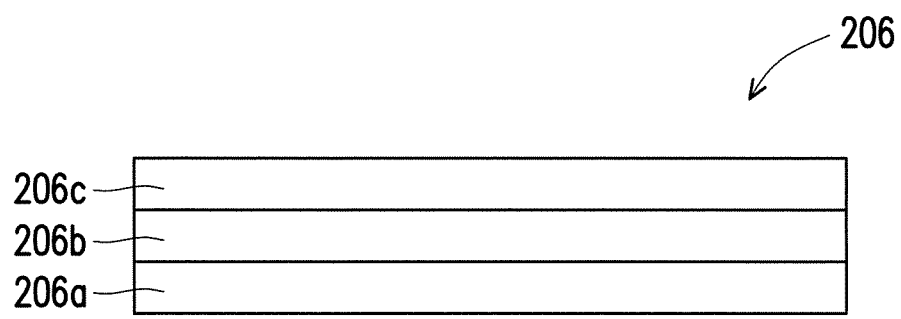
FIG. 4 is a schematic diagram of a breast milk absorbing pad according to an embodiment of the invention.

The two breast milk absorbing pads 206 are respectively located on the inner side of the two cup portions 202. In an embodiment, each of the two breast milk absorbing pads 206 include a contact layer 206a, an absorption layer 206b, and a waterproof layer 206c (as shown in FIG. 4). More specifically, the contact layer 206a is in contact with the breast skin, and can be a material having good breathability, such as nonwoven fabric, polyester fiber, or cotton fiber. The absorption layer 206b is located between the contact layer 206a and the waterproof layer 206c, and can be a material having good water absorption to absorb overflown breast milk. For instance, the material of the absorption layer 206b can be paper pulp, polymer absorber, or a combination thereof. The waterproof layer 206c can be a material impenetrable to liquid to prevent breast milk from wetting the undergarment and causing stains or damage. For instance, the waterproof layer 206c can be a polyethylene waterproofing membrane.

The sensing device 100 can be optionally disposed on the contact layer 206a, the absorption layer 206b, or the waterproof layer 206c in the two breast milk absorbing pads 206, and the invention is not limited thereto. In an embodiment, the sensing device 100 can be disposed on the absorption layer 206b of the two breast milk absorbing pads 206 such that the sensing device 100 is not in direct contact with the breast skin, and will not cause discomfort to the user.

The sensing devices 100 are respectively located on the two breast milk absorbing pads 206 to measure the resistance or conductivity of breast milk to calculate the ion concentration of breast milk. Therefore, the nursing bra 200 can monitor the ion concentration of breast milk at any time, such that women can know when to perform cleaning or empty the breast milk during the lactation stage to effectively prevent symptoms of lactiferous duct blockage or mastitis. More specifically, the concentration range of the sodium ions in breast milk is between 10 mmol/L and 25 mmol/L; the concentration range of the potassium ions in breast milk is between 5 mmol/L and 20 mmol/L; a ratio of sodium ions concentration to potassium ions concentration less than 0.6 ($Na^+/K^+<0.6$) is normal, and a ratio of sodium ions concentration to potassiums ion concentration greater than 1 ($N^+/K^+>1$) is abnormal, and at this point, signs of lactiferous duct blockage or mastitis may be present, and cleaning or emptying of breast milk needs to be performed as soon as possible.

A plurality of sensing devices 100 can be disposed on the breast milk absorbing pads 206 to increase the accuracy of the sensing devices 100. The sensing devices 100 can optionally be uniformly distributed on the breast milk absorbing pads 206 or concentrated at the locations corresponding to breast milk secretion on the two breast milk absorbing pads 206, and the invention is not limited thereto.

It should be mentioned that, the ion concentration ranges of human sweat and breast milk are different, and therefore the issue of mutual interference can be prevented. More specifically, the concentration range of the sodium ions in human sweat is between 26 mmol/L and 44 mmol/L; the concentration range of the potassium ions in human sweat is between 5.1 mmol/L and 8.2 mmol/L; and the concentration of the sodium ions in physiological saline (0.9 g of NaCl dissolved in 1 L of water) is 154 mmol/L. Therefore, the concentration ranges of the sodium ions and potassium ions in breast milk are different from those in sweat and physiological saline, and therefore the nursing bra 200 can accurately determine whether signs of lactiferous duct blockage or mastitis are present and is not affected by sweat or physiological saline.

Still referring to FIG. 3, the manufacturing method of the nursing bra 200 of an embodiment of the invention includes the following steps. A nursing bra 200 is provided. Two breast milk absorbing pads 206 respectively cover the inner side of the two cup portions 202 of the nursing bra 200, wherein the two cup portions 202 are respectively located at the locations corresponding to human breasts. A sensing device 100 is respectively formed on the each of the two breast milk absorbing pads 206. A transmission device 208 is formed on the connecting portion 204 connected between the two cup portions 202, wherein the transmission device 208 is used for outputting the data of the sensing device 100.

It should be mentioned that, in the present embodiment, the method of forming the sensing device 100 includes a 3D printing method, an inkjet printing method, or a combination thereof. Therefore, the sensing device 100 can be readily formed on the non-planar breast milk absorbing pads 206 in the nursing bra 200, which is not readily achieved by a known semiconductor manufacturing method.

Based on the above, in the embodiments of the invention, a sensing device is formed by a 3D printing method, and therefore the sensing device is readily formed on the non-planar breast milk absorbing pads in the nursing bra. Moreover, the sensing device of the invention has the function of measuring the resistance value or conductivity of a solution, and the ion concentration in the solution can be obtained after conversion. Therefore, by integrating the sensing device in the nursing bra, the concentration of sodium ions or potassium ions in breast milk can be monitored at any time, such that women can know when to perform cleaning or empty the breast milk during the lactation stage to effectively prevent symptoms of lactiferous duct blockage or mastitis.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A sensing device for sensing an ion concentration of a solution, the sensing device comprising:
   a first substrate, wherein a material thereof comprises cellulose;
   a second substrate, located on the first substrate;
   a sensing layer, located on the second substrate;
   an insulating layer located between the second substrate and the sensing layer;
   two electrodes, separately disposed on the sensing layer to expose the sensing layer and bring the solution in contact with the sensing layer so as to measure the resistance value of the solution through the sensing layer and convert the resistance value into the ion concentration of the solution;
   a modified layer disposed on the sensing layer between the two electrodes; and
   a protective layer covering top surfaces and sidewalls of the two electrodes, wherein the protective layer exposes the sensing layer between the two electrodes,
   wherein the sensing layer is located between the second substrate and the two electrodes.

2. The sensing device of claim 1, wherein the ion comprises a sodium ion, a potassium ion, or a combination thereof.

3. The sensing device of claim 2, wherein a concentration range of the sodium ion is between 10 mmol/L and 25 mmol/L.

4. The sensing device of claim 2, wherein a concentration range of the potassium ion is between 5 mmol/L and 20 mmol/L.

5. The sensing device of claim 1, wherein a material of the sensing layer comprises a metal oxide.

6. The sensing device of claim 5, wherein the metal oxide comprises tin oxide, zinc oxide, tungsten oxide, titanium oxide, iron oxide, chromium oxide, indium tin oxide, indium zinc oxide, or a combination thereof.

7. A nursing bra suitable for sensing an ion concentration of breast milk, the nursing bra comprising:
   two cup portions, respectively disposed at locations corresponding to human breasts;
   a connecting portion, connected between the two cup portions;
   two breast milk absorbing pads, respectively located on an inner side of the two cup portions; and
   two of the sensing devices of claim 1, respectively disposed on the two breast milk absorbing pads.

8. The nursing bra of claim 7, further comprising a transmission device, located on an inner side of the connecting portion, wherein the transmission device is used to output a data of the two sensing devices.

9. A manufacturing method of a sensing device, wherein the sensing device is suitable for sensing an ion concentration of a solution, and the manufacturing method of a sensing device comprising:
   providing a first substrate, wherein a material of the first substrate comprises cellulose;
   forming a second substrate on the first substrate;
   forming an insulating layer on the second substrate;
   forming a sensing layer on the insulating layer;

forming two electrodes separated from each other on the sensing layer to expose the sensing layer and bring the solution in contact with the sensing layer so as to measure a resistance value of the solution through the sensing layer and convert the resistance value into the ion concentration of the solution;

forming a modified layer on the sensing layer between the two electrodes; and forming a protective layer covering top surfaces and sidewalls of the two electrodes, wherein the protective layer exposes the sensing layer between the two electrodes, wherein the sensing layer is formed between the second substrate and the two electrodes.

10. The manufacturing method of a sensing device of claim 9, wherein a method of providing the first substrate, a method of forming the second substrate, a method of forming the sensing layer, and a method of forming the two electrodes comprises 3D printing.

11. A manufacturing method of a nursing bra, wherein the nursing bra is suitable for sensing an ion concentration of breast milk, and the manufacturing method of the nursing bra comprising:

disposing two breast milk absorbing pads respectively on an inner side of two cup portions of the nursing bra, wherein the two cup portions are respectively located at locations corresponding to human breasts;

performing the manufacturing method of a sensing device of claim 9 respectively on the two breast milk absorbing pads to form two sensing devices.

12. The manufacturing method of a nursing bra of claim 11, further comprising:

disposing a transmission device on an inner side of a connecting portion connected between the two cup portions, wherein the transmission device is used to output a data of the two sensing devices.

13. A sensing device for sensing an ion concentration of a solution, the sensing device comprising:

a first substrate, wherein a material thereof comprises cellulose;

a second substrate, located on the first substrate;

a sensing layer, located on the second substrate; and two electrodes, separately disposed on the sensing layer to expose the sensing layer and bring the solution in contact with the sensing layer so as to measure the resistance value of the solution and convert the resistance value into the ion concentration of the solution, wherein a material of the sensing layer comprises a metal oxide.

14. A nursing bra suitable for sensing an ion concentration of breast milk, the nursing bra comprises:

two cup portions, respectively disposed at locations corresponding to human breasts;

a connecting portion, connected between the two cup portions;

two breast milk absorbing pads, respectively located on an inner side of the two cup portions; and two of the sensing devices of claim 13, respectively disposed on the two breast milk absorbing pads.

* * * * *